United States Patent
De Haan et al.

(10) Patent No.: US 11,547,365 B2
(45) Date of Patent: Jan. 10, 2023

(54) SYSTEM AND METHOD FOR SKIN DETECTION OF A HUMAN SUBJECT

(71) Applicant: KONINKLIJKE PHILIPS N.V., Eindhoven (NL)

(72) Inventors: Gerard De Haan, Helmond (DE); Willem Verkruijsse, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1043 days.

(21) Appl. No.: 16/091,548

(22) PCT Filed: Apr. 6, 2017

(86) PCT No.: PCT/EP2017/058174
§ 371 (c)(1),
(2) Date: Oct. 5, 2018

(87) PCT Pub. No.: WO2017/178310
PCT Pub. Date: Oct. 19, 2017

(65) Prior Publication Data
US 2019/0104999 A1 Apr. 11, 2019

(30) Foreign Application Priority Data
Apr. 13, 2016 (EP) .................................. 16165099

(51) Int. Cl.
*A61B 5/00* (2006.01)
*A61G 11/00* (2006.01)
(Continued)

(52) U.S. Cl.
CPC ........ *A61B 5/7264* (2013.01); *A41D 13/1236* (2013.01); *A61B 5/0075* (2013.01);
(Continued)

(58) Field of Classification Search
CPC ... A61B 5/7264; A61B 5/0075; A61B 5/0077; A61B 5/1032; A61B 5/441;
(Continued)

(56) References Cited

U.S. PATENT DOCUMENTS 6,673,007 B2 1/2004 Salmon
2008/0102724 A1 5/2008 Frankel
(Continued)

FOREIGN PATENT DOCUMENTS

JP 2000328441 11/2000

OTHER PUBLICATIONS

Van Gastel, et al., "Motion robust remote-PPG in infrared", IEEE, Tr. On Biomedical Engineering, vol. 62, No. 5, 2015, pp. 1425-1433.
(Continued)

*Primary Examiner* — Gabriel I Garcia

(57) ABSTRACT

The present invention relates to a system and method of skin detection of a human subject using a textile product. The textile product (10, 31, 43) is made from or comprising textile including near-infrared, NIR, absorbing pigments. It supports and/or partially covers the human subject while skin detection and/or detection/monitoring vital signs of the human subject is carried out. A increased contrast between the textile product and skin in the NIR wavelength range is thus achieved.

12 Claims, 3 Drawing Sheets

(51) Int. Cl.
 *A61G 7/05* (2006.01)
 *G06T 7/90* (2017.01)
 *G06V 40/10* (2022.01)
 *A41D 13/12* (2006.01)
 *A61B 5/103* (2006.01)
 *D06P 1/00* (2006.01)

(52) U.S. Cl.
 CPC .......... *A61B 5/0077* (2013.01); *A61B 5/1032* (2013.01); *A61B 5/441* (2013.01); *A61G 7/05* (2013.01); *A61G 11/00* (2013.01); *D06P 1/004* (2013.01); *G06T 7/90* (2017.01); *G06V 40/10* (2022.01); *A61B 2503/045* (2013.01); *A61B 2576/00* (2013.01); *A61G 2203/30* (2013.01)

(58) Field of Classification Search
 CPC . A61B 2503/045; A61B 2576/00; G06T 7/90; G06V 40/01; A41D 13/1236; A61G 7/05; A61G 11/00; A61G 2203/30; D06P 1/004
 USPC ........................................................ 382/173
 See application file for complete search history.

(56) References Cited

U.S. PATENT DOCUMENTS

| | | |
|---|---|---|
| 2008/0116401 A1 | 5/2008 | Rice |
| 2009/0238333 A1* | 9/2009 | Matousek .............. G01N 21/65 |
| | | 356/301 |
| 2011/0167572 A1 | 7/2011 | Jarvis |
| 2012/0026308 A1 | 2/2012 | Johnson |
| 2012/0286177 A1 | 11/2012 | Cliver |
| 2014/0086462 A1 | 3/2014 | Shan |
| 2014/0180132 A1 | 6/2014 | Shan |
| 2014/0247478 A1 | 9/2014 | Bates |
| 2016/0066034 A1* | 3/2016 | Hicks ............... H04N 21/44218 |
| | | 725/12 |
| 2017/0314185 A1* | 11/2017 | Wijesena ............... D06M 11/45 |
| 2019/0192710 A1* | 6/2019 | Andersson ............. H05B 47/16 |

OTHER PUBLICATIONS

Goudarzi, et al., "Camouflage of cotton fabrics in visible and NIR region using three selected vat dyes", Apr. 2014, Color Research & Application (vol. 39, issue 2, pp. 200-207.

* cited by examiner

SYSTEM AND METHOD FOR SKIN DETECTION OF A HUMAN SUBJECT

CROSS REFERENCE TO RELATED APPLICATIONS

This application is the U.S. National Phase application under 35 U.S.C. § 371 of International Application No. PCT/EP2017/058174, filed Apr. 6, 2017, published as WO 2017/178310 on Oct. 19, 2017, which claims the benefit of European Patent Application Number 16165099.9 filed Apr. 13, 2016. These applications are hereby incorporated by reference herein.

FIELD OF THE INVENTION

The present invention relates to a system and method for skin detection of a human subject using such a textile product. Still further, the present invention relates to the use of such a textile product and to an incubator.

BACKGROUND OF THE INVENTION

Health monitoring is traditionally present in the hospital, particularly the ICU and includes the monitoring of vital signs like EEG, ECG, pulse-rate, respiratory rate, blood-oxygenation level, blood pressure, etc. Also sleep laboratories acquire information about sleeping subjects using actigraphy and electromyography, additionally to some of the other vital signs. These application areas often involve multiple sensors attached to the body of the patient, some of which may be wireless and others wired, restricting the freedom to move or the quality of sleep of the patient, in addition to causing discomfort and possible skin-damage.

Video Health Monitoring is recently emerging as a promising unobtrusive alternative for an increasing number of the above health indicators, not the least driven by the strong wish to reduce the burden caused by current techniques to (pre-term) neonates and patients with extensive skin damage, e.g. due to burns.

Clearly, Video Health Monitoring, due to its unobtrusive character, adds to patient comfort even in cases where no real damage is done by the current technology. However, also new application fields emerge in the consumer domain, as simpler derived methods may run on consumer platforms like laptops, tablets and mobile phones, or on embedded platforms inside equipment used for exercise in the gym.

Video Health Monitoring is also emerging for use in analyzing the human skin, in particular with relevance for cosmetic industry (e.g. moisturizers advice) and dermatology (e.g. melanoma detection). Various diseases may be diagnosed from motion in video sequences, like Periodic Leg Movements, Delirium, while video analysis may reveal information about body posture with relevance in baby monitors to prevent Sudden Infant Death. Such motions that can be analyzed in order to extract the health condition of a patient are also understood as vital signs.

Consequently, there is a very broad application domain for Video Health Monitoring ranging from beauty product, the gym, consumer home-healthcare including baby-monitoring, sleep-center, the General Ward, the Intensive Care Unit, to the highly specialized Neonatal Intensive Care Unit and burn-center.

While a promising new field, many challenges have to be overcome. For instance, in camera based monitoring of vital signs, e.g. using remote photo-plethysmography (rPPG) important for a reliable measurement is a correct detection of a skin region of the subject to be monitored.

Textile products comprising NIR absorbing properties are e.g. disclosed in US 2012/286177 A1, US 2011/167572 A1 and US 2008/102724 A1.

SUMMARY OF THE INVENTION

It is an object of the present invention to provide a solution for improving the detection of skin, in particular the differentiation between skin and other elements adjacent to skin areas, like various textile products and backgrounds.

In a first aspect of the present invention a textile product is presented that is configured for supporting and/or partially covering a human subject, said textile product being made from or comprising textile including near-infrared, NIR, absorbing pigments.

In a further aspect of the present invention an incubator is presented, said incubator comprising a mattress and/or bedding, wherein said mattress and/or said bedding is at least partly covered with and/or made from a textile product as disclosed herein.

In a first aspect of the present invention a system and a corresponding method for skin detection of a human subject are presented, said system comprising:

a detection unit for detecting near-infrared light, NIR, light from a scene including at least part of the human subject, a classifier for classifying one or more regions of interest of said scene as skin region of a living being or as non-skin region based on the strength and/or the color of the light detected from the respective region of interest, and a textile product supporting and/or partially covering the human subject, said textile product being made from or comprising textile including near-infrared, NIR, absorbing pigments. In a further aspect of the present invention an incubator is presented, said incubator comprising a mattress and/or bedding, wherein said mattress and/or said bedding is at least partly covered with and/or made from a textile product being made from or comprising textile including near-infrared, NIR, absorbing pigments.

In a further aspect of the present invention the use of a textile product as disclosed herein is presented, said textile product being configured for supporting and/or partially covering a human subject while performing skin detection of a human subject by a system or a method as disclosed herein, said textile product being made from or comprising textile including near-infrared, NIR, absorbing pigments.

Preferred embodiments of the invention are defined in the dependent claims. It shall be understood that the claimed method, system, incubator and use have similar and/or identical preferred embodiments as the claimed system, in particular as defined in the dependent claims and as disclosed herein.

The present invention is based on the finding that differentiating between skin and other elements, e.g. when registered by a camera (as detection unit of the disclosed system), is particularly hard if radiation in the near-infrared (NIR) range is used and evaluated, as is e.g. typical for usage during sleep and monitoring of neonates who have to be in low lighting conditions (around 1 lux) for substantial parts of the day. The difficulty arises from the relatively flat reflection spectra of the skin and other materials in the NIR range which makes it hard to discriminate on basis of spectral signature. To solve this problem it is proposed to make use of the proposed textile product(s), particularly in the area close to the subject's skin that shall be detected. In this way, an increased contrast (preferably a maximum contrast) between the textile product and the subject's skin (from which e.g. vital signs shall be detected) is achieved in the NIR range. The high contrast between the skin and the (main) other elements in the surrounding, e.g. in the camera view, facilitates an easy skin detection at low (processing) cost.

The present invention can advantageously be used in a system and method for skin detection, particular in a system and method for camera-based vital signs monitoring, for instance in the NICU and other medical care settings such as hospitals, houses for the elderly, etc., which involve a highly controlled environment. Further, for improving the monitoring of neonates in the NICU, the textile products may be used in the incubator, e.g. for the bedding, sheets, pillowcases, blankets, clothing etc., to obtain a maximum contrast with the infants' skin.

According to an embodiment said NIR-absorbing pigments and/or said textile have an absorption spectrum of NIR radiation that is significantly different from the absorption spectrum of NIR radiation of human skin. Thus, at least the pigments show an absorption spectrum that differentiates it from human skin in the NIR range. Since skin has a rather flat absorption spectrum in NIR, the absorption spectrum may e.g. have an absorption dip or notch somewhere in the NIR range or may e.g. be tilted compared to the absorption spectrum of skin (skin typically has a slightly increasing reflection for longer wavelengths; if the pigments have a clearly decreasing reflection they can be distinguished from skin).

In another embodiment said NIR-absorbing pigments and/or said textile have an absorption (sometimes also called absorption rate) of NIR radiation that is higher than the NIR absorption of human skin, in particular an absorption of at least 50%, at least 75% or at least 90%, or an absorption of NIR radiation that is lower than the NIR absorption of human skin, in particular an absorption of less than 35% or less than 10%. This clearly allows distinguishing the textile product from skin.

Advantageously, said NIR-absorbing pigments and/or said textile have said NIR absorption at a wavelength or wavelength interval in the wavelength range of 650-1100 nm, in particular of 620-1200 nm. This wavelength rage is e.g. of interest for vital signs detection by used of remote PPG, as generally known in the art and described in many documents, e.g. in M. van Gastel, S. Stuijk and G. de Haan, "Motion robust remote-PPG in infrared", IEEE, Tr. On Biomedical Engineering, Vol. 62, No. 5, 2015, pp. 1425-1433.

In another embodiment said textile has a reflectivity spectrum of NIR radiation that is significantly different from the reflectivity spectrum of NIR radiation of human skin. The textile product may particularly have a reflectance (sometimes also called reflectance rate) of NIR radiation that is lower than the reflectance of human skin, in particular lower than 50%, lower than 25% or lower than 10%, or a reflectance of NIR radiation that is higher than the reflectance of human skin, in particular higher than 65% or higher than 80%, particularly at a wavelength or wavelength interval in the wavelength range of 650-1100 nm, in particular of 620-1200 nm. This also allows clearly distinguishing the textile product from skin.

In a practical implementation the textile may be treated with dye containing NIR-absorbing pigments. For instance, a dye containing pigments with a relatively high absorption in the NIR range may be used, or a dye with a particular pseudo-color significantly different from human skin, but not necessarily absorbing very much in the complete NIR range may be used. Skin can then be detected from its "color" (in the NIR range) rather from the intensity, for which purpose a detection unit having at least two wavelength channels (e.g. an imaging unit such as a camera or photodetector having at least two photodetector elements) is used, as is e.g. used for vital signs detection and monitoring using rPPG.

In another embodiment the textile may be made from fibers containing or treated with NIR-absorbing pigments. Hence, the raw material of the textile (or cloth) may be pre-treated or manufactured accordingly, or fibers are used that inherently have the desired property.

If the contrast between skin and the other elements shall be further enhanced, a spatial contrast (in particular a pattern) with which the NIR-absorbing pigments are applied on the textiles may be used to further aid in providing contrast with skin. Hence, in another embodiment of the textile product, the NIR-absorbing pigments are included in said textile in a patterned fashion, in particular as dot pattern, line pattern, grid pattern or stripe pattern, including e.g. patterns like pigments (or dye with pigments)-no pigments-pigments, more pigments-less pigments-more pigments, type 1 pigments-type 2 pigments-type 1 pigments.

For practical use, e.g. in an incubator, but also in a hospital room, a care station or even at home for remote patient monitoring, said textile product may at least be part of bedding, sheet, pillowcase, blanket, clothing, pyjama and/or underwear.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

FIG. 1 shows a diagram illustrating the use of the textile product according to the present invention. In said embodiment the textile from which the textile product 10 (in this example a blanket) is made is treated with NIR-absorbing pigments such that the overall reflectance or the reflectance at a specific wavelength in the NIR-range of the textile product 10 becomes significantly lower than that of human skin 11 of the subject when illuminated with approximately the same NIR light levels. Algorithms may thus be employed that distinguish skin from textiles based on the apparent lightness of the structures (skin is significantly lighter than textiles).

Figure 1A:
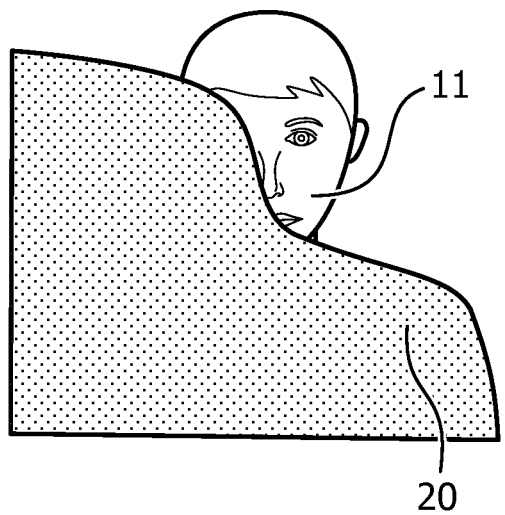
FIG. 1 shows a diagram illustrating the use of the textile product according to the present invention.
Figure 1B:
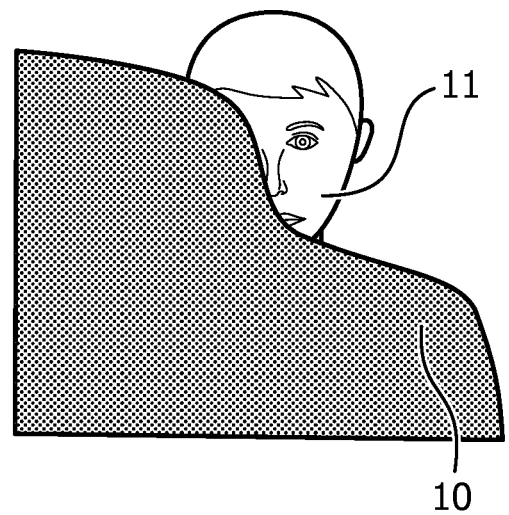

As shown in FIG. 1, in which the NIR channels are represented by normal grey color channels for illustration purposes only, the entire blanket is made "darker" with a NIR absorbing pigment resulting in a significantly darker tone than skin. In the situation shown in FIG. 1A a conventional blanket 20 is used showing a week contrast with skin 11 since at least some parts of the blanket 20 have colors similar to skin. In the situation shown in FIG. 1B a blanket 10 according to the present invention is used showing a strong contrast with skin 11.

Figure 2:
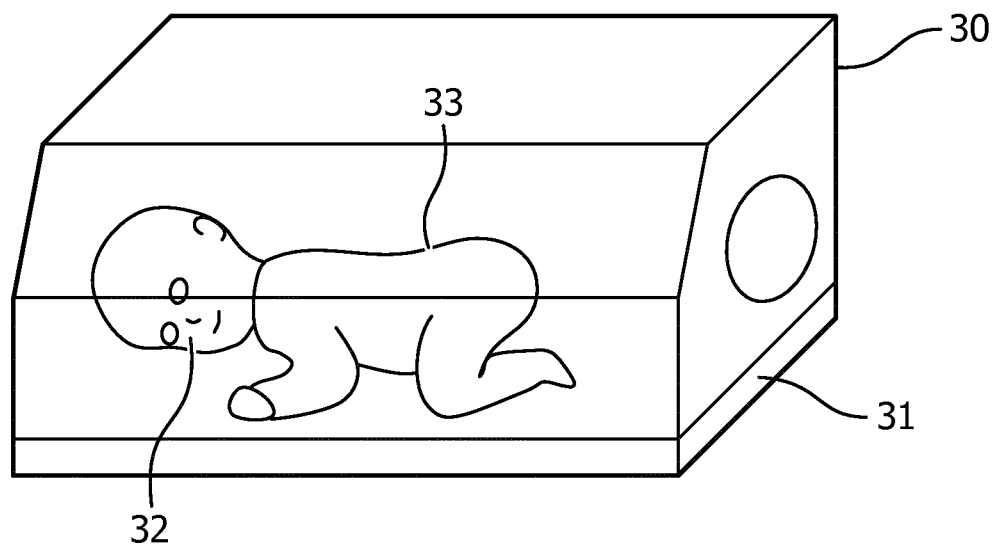
FIG. 2 shows an embodiment of an incubator according to the present invention.

FIG. 2 shows an embodiment of an incubator 30 according to the present invention. The incubator 30 comprises inter alia a mattress 31 (and e.g. bedding, etc.), which is at least partly covered with and/or made from a textile product according to the present invention. For instance, the mattress 31 may be covered by a mattress cover made from textile as disclosed herein, or the outer layer of the mattress 31 may be made from such textile. This provides that a good contrast between skin 32 of the baby 33 and the mattress 31 in the NIR range can be achieved.

Generally, according to the present invention a textile product shall be used for supporting and/or partially covering a human subject, which is made from or comprises textile including NIR absorbing pigments.

Hereby, the NIR-absorbing pigments and/or said textile may have an absorption spectrum of NIR radiation that is significantly different from the absorption spectrum of NIR radiation of human skin. The absorption of NIR radiation may be higher than the NIR absorption of human skin, in particular of at least 50%, in particular of at least 75% or at least 90%. Alternatively, the absorption of NIR radiation may be lower than the NIR absorption of human skin, in particular an absorption of less than 35% or less than 10%.

In other embodiments the textile product may be configured such that the textile has a reflectivity spectrum of NIR radiation that is significantly different from the reflectivity spectrum of NIR radiation of human skin. The reflectance of NIR radiation may be lower than the reflectance of human skin, in particular lower than 50%, in particular lower than 25% or lower than 10%. Alternatively, the reflectance of NIR radiation may be higher than the reflectance of human skin, in particular higher than 65% or higher than 80%.

These different properties as to absorption and reflectance of the NIR-absorbing pigments and/or the textile are particularly of interest at one (or more) wavelength(s) or wavelength interval(s) in the wavelength range of 650-1100 nm, in particular of 620-1200 nm.

It shall be noted in this context that dark pigmented skin can have a quite low reflectance, even in the NIR wavelength range. If blood/melanin are the dominant pigments, the reflectance in the NIR wavelength range tends to be rather flat, but in light skin, water can add its signature to the reflectance and drop down the reflectance towards 100 nm. Water can also push down the reflectance for larger wavelengths so that the NIR-absorbing pigments may actually be featuring decreasing absorption. Hence, different textile products may actually be used in practical application depending on whether the subject has light or dark skin.

Figure 3:
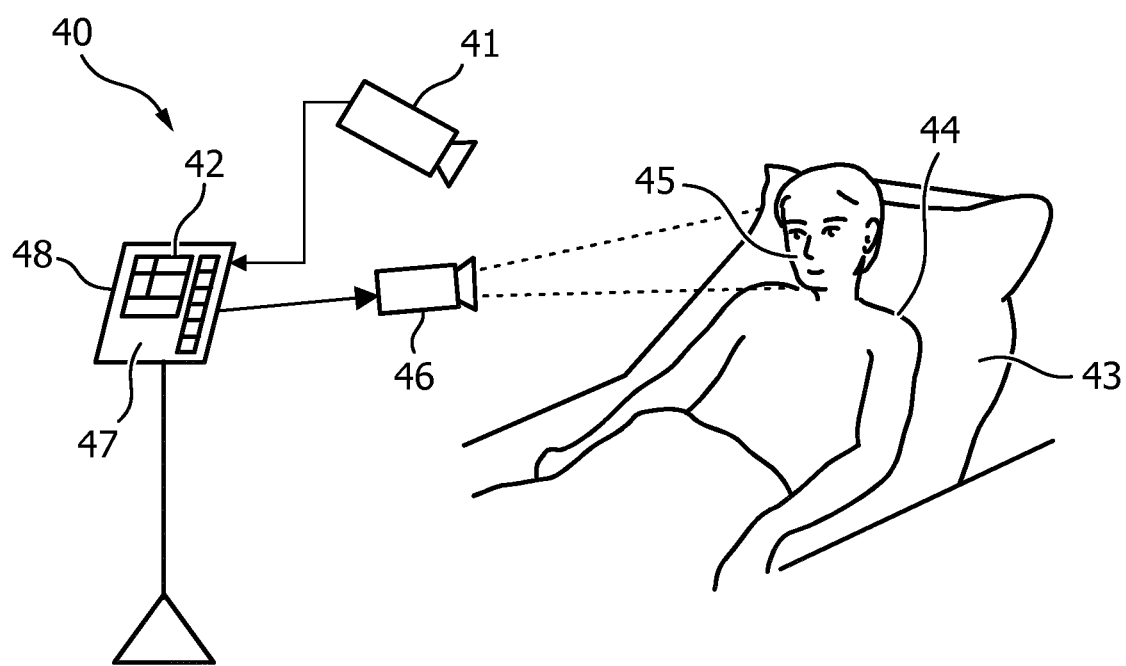
FIG. 3 shows a schematic diagram of an embodiment of a system according to the present invention.

FIG. 3 shows a schematic diagram of an embodiment of a system 40 according to the present invention. In a basic embodiment the system 40 may be configured for skin detection of a human subject. In a more elaborate embodiment the system may also be used for vital signs detection and/or monitoring using remote PPG.

In a basic embodiment the system 40 comprises a detection unit 41, e.g. a camera or a photodetector, with one or more color channels (at least one color channel in the NIR) for detecting NIR light from a scene including at least part of a human subject. The system 40 comprises further a classifier 42 for classifying one or more regions of interest of said scene as skin region of a living being or as non-skin region based on the strength and/or the color of the light detected from the respective region of interest. The classifier 42 may e.g. be a processor or computer that processes the detected NIR light, i.e. the output (e.g. electronic detection signals) of the detection unit 41. A textile product 43 (here the pillow case of the pillow) according to the present invention is used to support and/or partially cover the human subject 44 lying in a patient bed. In this exemplary embodiment the textile product 43 is a pillowcase, but may also e.g. be a bedding, sheet, blanket, clothing, pyjama and/or underwear, and is used to ensure that there is a sufficiently large contrast between the skin 45 (here of the subject's face) in the desired region(s) of interest and its environment, e.g. the surrounding textile products.

The system 40 may further be used for detecting and/or monitoring of vital signs (e.g. heart rate, respiration rate, SpO2, etc.) of the subject 44 from image data including a time sequence of image frames of the subject. The subject 44 in this example may be a patient in a hospital or other healthcare facility, but may also be a neonate or premature infant, e.g. lying in an incubator, or person at home or in a different environment, such as an athlete doing sports.

The detection unit 41 may include a camera (also referred to as detection unit or as camera-based or remote PPG sensor) for acquiring an image data (also called RGB images, which shall be understood as an image in the wavelength range of infrared (and preferably visual) light) of the scene, in particular for acquiring a sequence of image frames of the subject 44 over time, preferably including skin areas 45 of the subject 44 from which PPG signals can be derived. In an application the skin area 45 is preferably an area of the face, such as the cheeks or the forehead, but may also be another area of the body with visible skin surface, such as the hands or the arms.

The image frames captured by the detection unit 41 in this embodiment may particularly correspond to a video sequence captured by means of an analog or digital photosensor, e.g. in a (digital) camera. Such a camera usually includes a photosensor, such as a CMOS or CCD sensor, which may also operate in a specific spectral range (visible, nIR) or provide information for different spectral ranges, particularly enabling the extraction of PPG signals. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the person. Thereby, an image pixel may correspond to one photosensitive element of a photo-detector and its (analog or digital) output or may be determined based on a combination (e.g. through binning) of a plurality of the photosensitive elements.

When using a camera as detection unit 41 the system 40 may further optionally comprise an illumination unit 46 (also called illumination source or light source or electromagnetic radiator), such as a lamp or LED, for illuminating/irradiating a region of interest, such as the skin of the patient's face (e.g. part of the cheek or forehead), with light, for instance in a predetermined wavelength range or ranges (e.g. in the infrared and, optional red and/or green wavelength range(s)). The light reflected from said region of interest in response to said illumination is detected by the camera. In another embodiment no dedicated light source is provided, but ambient light is used for illumination of the subject 44. From the reflected light only light in a desired wavelength ranges (e.g. infrared light, or light in a sufficiently large wavelength range covering at least two wavelength channels) may be detected and/or evaluated.

The device 47, e.g. a processor or computer including the classifier 42, may further be connected to an interface 48 for displaying the determined information and/or for providing medical personnel with an interface to change settings of the device 47, the camera 41, the illumination unit 46 and/or any other parameter of the system 40. Such an interface 48 may comprise different displays, buttons, touchscreens, keyboards or other human machine interface means.

A system 40 as illustrated in FIG. 3 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, a wearable, a handheld device like a smartphone, or the like. The uni- or bidirectional communication between the device 47, the camera 41 and the interface 48 may work via a wireless or wired communication interface. Other embodiments of the present invention may include a device 47, which is not provided stand-alone, but integrated into the camera 41 or the interface 48.

Figure 4A:
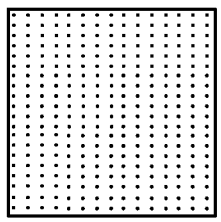
FIG. 4 shows diagrams of various patterns of NIR-pigments as used in different embodiment of the textile product according to the present invention.
Figure 4B:
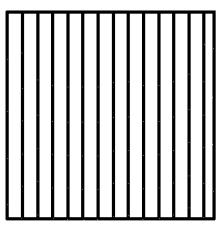
Figure 4C:
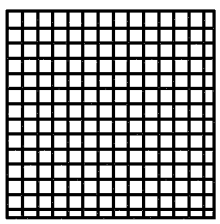
Figure 4D:
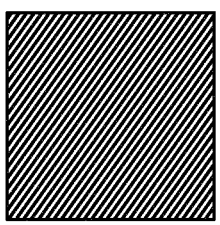
Figure 4E:
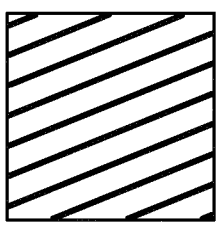

In another embodiment textiles are manufactured with NIR-absorbing pigments applied (sprayed, woven in, etc.) in a patterned fashion. Dots, lines, or any patterned application of NIR pigments on the textiles that can be relatively easily recognized as manmade (i.e. non-skin) may be used to aid in distinguishing skin from textiles. Example patterns are illustrated in FIG. 4, in which FIG. 4A shows a dot pattern, FIG. 4B shows a first line pattern, FIG. 4C shows a grid pattern, FIG. 4D shows a second line pattern and FIG. 4E shows a third line pattern. While a dot pattern and a line pattern may find similarities with human skin, this is very unlikely for a grid-like pattern.

In another embodiment, to retrofit existing textiles, NIR absorber treated threads may be sown in these textiles, e.g. at regular distances, preferably in a grid like manner to avoid possible similarities with hairs that could provide similar spatial frequencies and alignment.

For evaluation an FFT transform of an image acquired by the detection unit may be generated. FFT images may provide better contrast to distinguish skin from NIR treated textiles because regularities show up as distinct peaks. Thus, if an algorithm based on lightness or a periodic pattern does not provide sufficient contrast, a Fourier transformed image may be used to analyze the peak contrast in these images which will likely be much higher in the NIR/pattern treated textile than in the skin areas.

By use of patterns of NIR absorbers, the absorption characteristics of the pigments need not necessarily be so much different from those of the non-treated textile parts. Patterns of small contrasts are relatively easily detected compared to an overall darker homogeneous textile. If a simple algorithm (e.g. using trained feature/pattern detection of the NIR pattern) may not detect the pattern of NIR pigments, a local Fourier transform of the image in the spatial domain would feature distinct peaks in the case of a regular pattern at (known) spatial frequencies. The found spatial frequencies may be slightly smaller when the textile is 'seen' by the camera under an angle. Nevertheless, local inspection using FFT will provide a distribution of peaks that is consistent with the 'known' spatial frequencies of the applied NIR pigments.

In the unlikely case that skin with hairs would also feature such peaks (after FFT in the spatial domain), the pattern may be applied in two directions to break the similarity with hairs on skin which are typically aligned in one dominant direction. This also provides an additional advantage in the sense of needing less NIR-absorbing pigments to achieve the same contrast. Further, it has been proven that folds in textile will still show significant periodicity (and thus contrast with skin) if a periodicity in more than one direction is applied.

Thus, in summary, according to the present invention a pigment/dye in the textiles (bedding/mattress) e.g. of an incubator (or bed in other applications) with an absorption in the NIR that is sufficiently different from the absorption of human skin in the NIR, or at least an absorption spectrum which makes it easy to distinguish from that of the skin of human subject, is proposed.

The present invention may be applied for camera-based measurement of pulse rate, respiration and SpO2 in patient monitoring. The contactless monitoring with a camera is assumed to be highly relevant for premature babies with very sensitive skin in NICUs.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A system for skin detection of a human subject, said system comprising:
   a detection unit for detecting near-infrared light, NIR, light from a scene including at least part of the human subject,
   a textile product for supporting and/or partially covering the human subject, said textile product being made from or comprising textile including NIR-absorbing pigments, and
   a classifier for classifying one or more regions of interest of said scene as skin region of a living being or as non-skin region based on the strength and/or the color of the light detected from the respective region of interest, said one or more regions of interest of said scene including one or more regions of said scene including said textile product and one or more regions of said scene not including said textile product.

2. The system as claimed in claim 1,
   wherein said NIR-absorbing pigments and/or said textile have an absorption spectrum of NIR radiation that is significantly different from the absorption spectrum of NIR radiation of human skin.

3. The system as claimed in claim 1,
   wherein said NIR-absorbing pigments and/or said textile have an absorption of NIR radiation that is higher than the NIR absorption of human skin, in particular an absorption of at least 50%, in particular of at least 75% or at least 90%, or an absorption of NIR radiation that is lower than the NIR absorption of human skin, in particular an absorption of less than 35% or less than 10%.

4. The system as claimed in claim 3, wherein said NIR-absorbing pigments and/or said textile have said NIR absorption at a wavelength or wavelength interval in the wavelength range of 650-1100 nm, in particular of 620-1200 nm.

5. The system as claimed in claim 1, wherein said textile has a reflectivity spectrum of NIR radiation that is significantly different from the reflectivity spectrum of NIR radiation of human skin.

6. The system as claimed in claim 1, wherein said textile has a reflectance of NIR radiation that is that is lower than the reflectance of human skin, in particular lower than 50%, in particular lower than 25% or lower than 10%, or a reflectance of NIR radiation that is that is higher than the reflectance of human skin, in particular higher than 65% or higher than 80%.

7. The system as claimed in claim 6, wherein said textile has said reflectance at a wavelength or wavelength interval in the wavelength range of 650-1100 nm, in particular of 620-1200 nm.

8. The system as claimed in claim 1, wherein said textile is treated with dye containing NIR-absorbing pigments.

9. The system as claimed in claim 1, wherein said textile is made from fibers containing or treated with NIR-absorbing pigments.

10. The system as claimed in claim 1, wherein said NIR-absorbing pigments are included in said textile in a patterned fashion, in particular as dot pattern, line pattern, grid pattern or stripe pattern.

11. The system as claimed in claim 1, wherein said textile product is at least part of bedding, sheet, pillowcase, blanket, clothing, pajama and/or underwear.

12. A method for skin detection of a human subject, said method comprising:
    detecting near-infrared light, NIR, light from a scene including at least part of the human subject, wherein the human subject is supported and/or partially covered by a textile product, said textile product being made from or comprising textile including NIR-absorbing pigments, and
    classifying one or more regions of interest of said scene as skin region of a living being or as non-skin region based on the strength and/or the color of the light detected from the respective region of interest, said one or more regions of interest of said scene including one or more regions of said scene including said textile product and one or more regions of said scene not including said textile product.

* * * * *